United States Patent [19]

Finkel et al.

[11] Patent Number: 5,976,786

[45] Date of Patent: Nov. 2, 1999

[54] SCREENING METHODS FOR THE IDENTIFICATION OF COMPOUNDS THAT MODULATE APOPTOSIS IN IMMUNODEFICIENCY VIRUS INFECTED CELLS

[75] Inventors: Terri H. Finkel, Englewood; Carolyn Casella, Denver, both of Colo.

[73] Assignee: National Jewish Medical and Research Center, Denver, Colo.

[21] Appl. No.: 08/774,269

[22] Filed: Dec. 27, 1996

Related U.S. Application Data

[60] Provisional application No. 60/009,460, Dec. 29, 1995.

[51] Int. Cl.$^6$ .................................................... C12Q 1/70
[52] U.S. Cl. ................................................ 435/5; 435/375
[58] Field of Search .............................. 435/5, 7.21, 7.24, 435/375

[56] References Cited

FOREIGN PATENT DOCUMENTS

WO94/21806  9/1994  WIPO.

OTHER PUBLICATIONS

Pantaleo et al., 1995, "Apoptosis in HIV infection", Nature Med. 1:118–120.
Finkel et al., 1994, "Indirect mechanisms of HIV pathogenesis: how does HIV kill T cells?", Curr. Opin. Immunol. 6:605–615.
Finkel et al., 1995, "Apoptosis occurs predominantly in bystander cells and not in productively infected cells of HIV– and SIV–infected lymph nodes", Nature Med. 1:129–134.
Balotta et al., 1993, J. of Virol., 67(7):4409–4414.
Finkel et al., 1994, Current Opinion in Immunol., 6:605–615.
Hattori et al., 1990, Proc. Natl. Acad. Sci USA, 87:8080–8084.
Ho et al., 1995, Nature, 373:123–126.
Lang et al., 1993, J. of Virol., 67(2):902–912.
Levy et al., 1993, Cell, 72:541–550.
Ogawa et al., 1989, J. of Virol., 63(9):4110–4114.
Pantaleo et al., 1995, Nature Med., 1:118–120.
Rogel, 1995, J. of Virol., 69:882–888.
Shibata et al., 1990, J. of Virol., 64(2):742–747.
Xiping et al., 1995, Nature, 373:117–122.

Primary Examiner—Laurie Scheiner
Assistant Examiner—Jeffrey S. Parkin
Attorney, Agent, or Firm—Sheridan Ross P.C.

[57] ABSTRACT

Disclosed is a method to limit infection by an immunodeficiency virus. The method includes inhibiting an immunodeficiency virus protein which regulates apoptosis in cells. Also disclosed are methods to identify compounds that regulate cellular inhibitors of apoptosis in cells infected with an immunodeficiency virus and compounds identified thereby.

7 Claims, 2 Drawing Sheets

Fate of Infected and Uninfected CD4$^+$ T Cells in HIV Disease

SCREENING METHODS FOR THE IDENTIFICATION OF COMPOUNDS THAT MODULATE APOPTOSIS IN IMMUNODEFICIENCY VIRUS INFECTED CELLS

CROSS REFERENCE TO RELATED APPLICATION

The present application claims priority from U.S. Provisional Application Serial No. 60/009,460, filed Dec. 29, 1995.

GOVERNMENT RIGHTS

This invention was made in part with government support under AI-22903, AI-35513A, and AI-40003 awarded by the National Institutes of Health. The government has certain rights to this invention.

FIELD OF THE INVENTION

The present invention relates to a product capable of regulating cellular apoptosis resulting from immunodeficiency virus infection of a cell. The present invention also relates to therapeutic processes useful for treating immunodeficiency virus infection.

BACKGROUND OF THE INVENTION

It has been well-demonstrated that the human immunodeficiency virus (HIV) causes immunodeficiency in its host via an ongoing, virally induced process. Several studies have shown that HIV-infected individuals have actively replicating virus throughout all stages of disease. In addition, the level of viral RNA in the peripheral blood is a predictor of time until disease onset. In general, a higher viral load equates to faster disease progression. These observations suggest that the virus is responsible for the depletion of CD4$^+$ T cells and the destruction of the immune system. Less well understood is the mechanism by which HIV depletes its host of CD4$^+$ T cells. One hypothesis is that the virus may kill the CD4$^+$ T cell that it infects.

The lymphoid organs of infected individuals have been identified as the preferred location and continuous source of viral infection. In addition, the sensitive technique of polymerase chain reaction (PCR) has revealed high levels of virus in plasma and in peripheral blood cells throughout all stages of infection. These studies have provided evidence for a relationship between the levels of HIV RNA and disease progression, and argue strongly for a direct role of HIV replication in the pathogenesis of AIDS.

Studies of HIV cytopathicity using immortalized cell lines in culture, suggest that HIV infection directly kills CD4$^+$ T cells and that, depending on the HIV strain studied, this killing is either by single-cell lysis or by syncytia formation. Furthermore, in vitro cytopathicity of primary viral isolates (that is, virus cultured directly from an infected individual) increases with disease progression. Thus, the ability of the virus to kill cells in vitro correlates with the progression to AIDS.

Of particular relevance is the fact that T lymphoblasts infected by HIV in vitro have been shown to die, or more precisely, undergo programmed cell death or apoptosis. Apoptosis is a regulated mechanism of cell suicide that is critical to many physiological processes, including T cell development and normal immune function. Apoptosis of peripheral blood mononuclear cells (PBMCs) from HIV-seropositive individuals has been previously described. Interestingly, previous studies show apoptosis of CD4$^+$ T cells, and the majority of them also show apoptosis of CD8$^+$ T cells.

Apoptosis has been described in animal models of AIDS, including macaques infected with a pathogenic strain of SIV, cats infected with feline immunodeficiency virus, and mice with murine AIDS (MAIDS). In addition, studies have documented the absence of apoptosis and anergy in SIV-infected African green monkeys and in HIV-infected chimpanzees, animals that support long-term productive infection, but that do not develop AIDS-like disease. The correlation between apoptosis and the development of AIDS suggests an etiological role for apoptosis in AIDS.

Although fourteen years have passed since identification of human immunodeficiency virus-1 (HIV-1) as the cause of AIDS, it is still not known how HIV kills its primary target, the T cell that carries the CD4 antigen. Thus, there remains a need to develop an effective reagent and therapy for the treatment of HIV infected CD4$^+$ T cells.

SUMMARY

One embodiment of the present invention includes a method to limit infection by an immunodeficiency virus. The method includes inhibiting an immunodeficiency virus protein which regulates apoptosis in cells. Immunodeficiency viruses can include HIV, SIV and FIV; preferably, the immunodeficiency virus is HIV. HIV proteins which are inhibited by the present invention can be selected from the group of Vpr, Tat, Vif, Nef, Env, Gag, Vpu. In a preferred embodiment, immunodeficiency virus proteins are inhibited in infected CD4$^+$ or CD8$^+$ T cells.

In a further embodiment, the method can also include inhibiting non-immunodeficiency virus induced cellular apoptosis of uninfected bystander cells. For example, such a step can be conducted by regulating a compound selected from the group of Lck, cAMP, Protein kinase A, cdc2, cysteine proteases, proteins of the TNF receptor family, p53, Ras, Raf, MEKK1, Jun kinases, bcl-2 and oxygen radicals.

A further embodiment of the invention can also include administering an inhibitor of immunodeficiency virus replication. Such an inhibitor can be selected from the group of nucleoside analogues, non-nucleoside analogues, protease inhibitors, chemokine receptor inhibitors, antibodies specific for gp160, antibodies specific for gp120, CD4-gp160 protein complexes and gp120-CD4 protein complexes.

A further embodiment of the present invention includes a method to identify a compound that regulates a cellular inhibitor of apoptosis in cells infected with an immunodeficiency virus. The method includes contacting a putative regulatory compound with cells infected with an immunodeficiency virus in which, in the absence of the compound, apoptosis of the cells is inhibited. The method includes further assessing the ability of the putative regulatory compound to regulate apoptosis in cells. A difference in the rate of apoptosis between infected cells contacted with a compound and infected cells not in contact with a compound indicates that the compound regulates a cellular inhibitor of apoptosis in infected cells. The step of assessing the ability of the putative regulatory compound to regulate apoptosis can include a step selected from the group of (1) determining the extent of a morphological change in a cell selected from the group consisting of progressive contraction of cell volume with the preservation of the integrity of cytoplasmic organelles and condensation of chromatin; (2) determining the extent of DNA cleavage; and (3) determining membrane permeability. A further aspect of this embodiment of the invention includes compounds identified by the method.

Another embodiment of the present invention includes a method to identify a compound that regulates a cellular inhibitor of apoptosis in cells infected with immunodeficiency virus. The method includes contacting a putative regulatory compound with an immunodeficiency virus apoptosis inhibitor protein. The method further includes assessing the ability of the putative regulatory compound to regulate the activity of the immunodeficiency virus apoptosis inhibitor protein.

DETAILED DESCRIPTION OF THE INVENTION

The present invention relates to compounds which regulate immunodeficiency virus proteins that are inhibitors of apoptosis in infected cells and their use as a therapeutic reagents for the treatment of immunodeficiency virus infection. The present invention is predicated upon the unexpected discovery that in lymph node sections from ten HIV seropositive individuals in which HIV infection and apoptosis of T cells is occurring, apoptosis and productive infection are rarely seen in the same T cell. Thus, productive infection of T cells with HIV delays induction of apoptotic cell death. In addition, it has been discovered that apoptosis does occur in uninfected or bystander $CD4^+$ or $CD8^+$ T cells and not in the productively infected cells themselves. Without being bound by theory, it is believed that apoptosis is induced in uninfected bystander cells by cell-to-cell contact with an infected cell in the paracortical region and by follicular dendritic cell (FDC)-bound virions in the secondary follicle.

Figure 1:
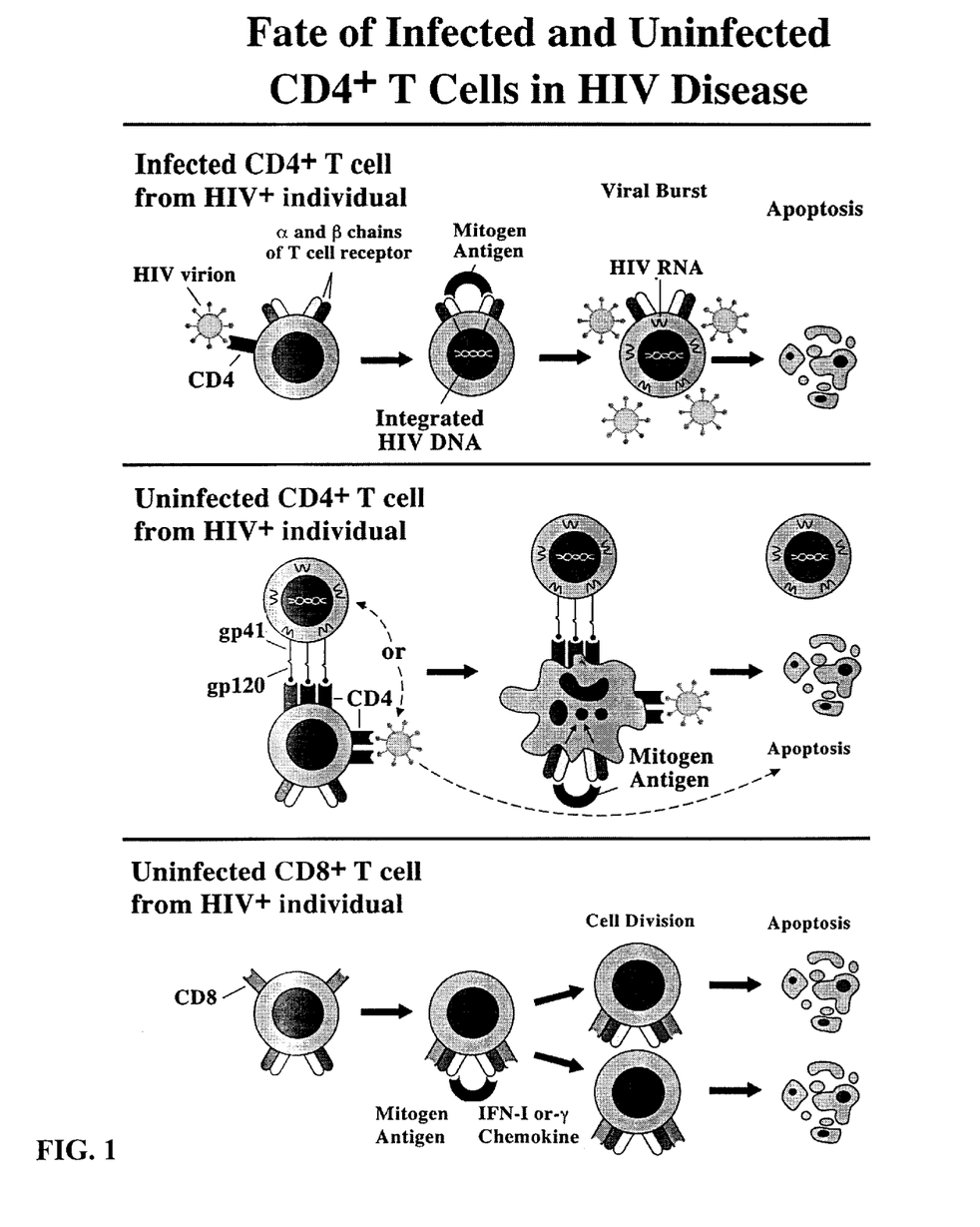
FIG. 1 is a schematic representation of the fate of infected and uninfected T cells in HIV disease.

Prior to the present invention, it was suggested that an HIV-infected cell is rapidly deleted in vivo. In contrast, the present inventors have shown that the virus acts to protect the infected cell from death, at least until the cell has produced high levels of virus, at which point the cell may die as a result of immune clearance or cytopathic effects of the virus. Without being bound by theory, the present inventors believe that death of uninfected cells occurs in vivo and is an important feature of the pathogenesis of immunodeficiency viruses. Another important feature of the pathogenesis of the virus is the decline in HIV-specific $CD8^+$ cytotoxic T lymphocytes (CTL), which occurs just before the rapid increase in viremia and accelerated decline of $CD4^+$ cells that signals progression to AIDS. The present inventors believe that the decline in $CD8^+$ T cell function which results in high virus production is instrumental in the decline in $CD4^+$ T cells. FIG. 1 is a schematic representation of the fate of HIV infected and uninfected T cells during HIV disease.

In one embodiment, of the present invention involves use of a compound capable of regulating a cellular inhibitor of apoptosis. Preferably, such a compound comprises a molecule capable of inhibiting a cellular inhibitor of apoptosis. As such, such a compound comprises an inhibitor of an inhibitor of cellular apoptosis. Apoptosis is a regulated form of cell suicide that is necessary for normal immune function and development. As used herein, apoptosis refers to a form of cell death that includes progressive contraction of cell volume with the preservation of the integrity of cytoplasmic organelles; condensation of chromatin (i.e., nuclear condensation), as viewed by light or electron microscopy; and/or DNA cleavage into nucleosome-sized fragments, as determined by centrifuged sedimentation assays. Cell death occurs when the membrane integrity of the cell is lost (e.g., membrane blebbing) with engulfment of intact cell fragments ("apoptotic bodies") by phagocytic cells. Apoptosis differs from necrosis in which cells swell and eventually rupture.

The present invention pertains to immunodeficiency viruses, including ones that are currently known and ones that are identified in the future. More particularly, the present invention pertains to human immunodeficiency virus ("HIV"), simian immunodeficiency virus ("SIV"), and feline immunodeficiency virus ("FIV"). Most preferably, the present invention pertains to HIV.

According to the present invention, compounds useful in the present process preferably include a molecule capable of interfering with a protein encoded by an immunodeficiency virus gene which is a cellular inhibitor of apoptosis in such a manner that the immunodeficiency virus-encoded protein is not active (i.e., cannot perform its normal function). More preferably, in the context of HIV, such a compound comprises a molecule capable of interfering with an HIV-encoded protein, including Vpr, Tat, Vif, Nef, Env, Gag, Vpu and CA and most preferably Vpr. Such HIV-encoded proteins are also referred to herein as HIV apoptosis inhibitor proteins.

HIV is one of the most complex viruses known to man. It is one of a family of retroviruses, and, like other retroviruses, contains two strands of RNA, as well as the proteins essential for packaging and replication, encoded by the gag, pol, and env genes. Several viral gene products affect the proliferative or activation status of cells in ways that may alter the cells' susceptibility to apoptosis. Such viral gene products which are embodied by the present invention include Vpr, Tat, Vif, Nef, Gag and Vpu. One embodiment of the present invention relates to compounds which regulate the Vpr protein. Vpr causes the infected cell to arrest in the G2 phase of the cell cycle by inhibiting activation of p34cdc2-cyclin B. This arrest in the cell cycle may increase the level of virus production by preventing the cell from reentering a resting/G0 state.

Another embodiment of the present invention relates to a compound which regulates the Tat protein. The Tat protein of HIV-1 has been shown to increase the level of Fas ligand (FasL) expression on T cells when added exogenously. The ability of Tat to increase FasL expression increases apoptotic death of uninfected cells expressing Fas. Tat is secreted from infected cells and upregulates FasL on uninfected cells. These cells can then either kill themselves by binding to Fas expressed on the same cell or kill another cell that has upregulated Fas. Soluble Tat has also been shown to cause the apoptosis of peripheral blood leukocytes (PBLs) by increasing the activity of cyclin A-dependent kinases. In addition, Tat has been shown to prevent apoptosis of an infected cell caused by serum withdrawal, and by TNF-A and anti-Fas antibodies. This function of Tat may help the cell survive in vivo in the absence of cytokines needed for the survival of $CD4^+$ T cells, or in the presence of apoptotic stimuli. Tat has also been reported to decrease transcription of p53 (a cellular tumor suppressor gene which can block cell proliferation and cause apoptosis) and to increase the transcription of bcl-2 (a cellular inhibitor of apoptosis). High levels of the bcl-2 protein can block apoptosis in response to several apoptotic stimuli. High levels of p53 can cause apoptosis if DNA damage is incurred, and p53 has been shown to repress bcl-2 expression. The reduction of p53 and the increase in bcl-2 are potent anti-apoptotic mechanisms of the virus. Furthermore, Tat has been shown to inhibit proliferation in response to antigen. This characteristic may help infected cells avoid apoptosis by preventing improper activation of the cell.

Another embodiment of the present invention relates to a compound which regulates Nef protein. Nef, a protein predominantly expressed early in HIV infection, reduces CD4 on the surface of the cell by displacing Lck and thereby allowing CD4 to be endocytosed. Envelope glycoprotein (Env) binds CD4 in the endoplasmic reticulum (ER) and sequesters it. In addition, Nef has also been reported to bind p53. In addition, Tat and Nef have been shown to downregulate surface expression of MHC class I. This may help the cell avoid being targeted by a CD8$^+$ cytotoxic T lymphocyte (CTL). Proliferation of PBL in response to IL-2 is greatly reduced in the presence of Nef. This may be due to the ability of Nef to downregulate the alpha chain of the IL-2R and to prevent the phosphorylation and activation of the tyrosine kinase Lck. In addition, Nef binds to pp44mapk/erkl and Hck, proteins which can mediate proliferative signals.

Yet another embodiment of the present invention relates to a compound which regulates Vpu protein. Vpu, which is expressed predominantly late in the life cycle, disrupts the CD4-Env complex in the ER, resulting in the release of Env and the degradation of CD4. The ability of HIV to reduce CD4 expression on the surface of the infected cell is important because of the role of CD4 in initiating apoptosis. The cytoplasmic tail of CD4 is required for induction of apoptosis by HIV and the ability of CD4 to bind the tyrosine kinase, Lck. Reduction of surface CD4 prevents infection by new viruses (superinfection interference), reduces the chance that soluble gp120 would bind the cell (which can cause apoptosis of a cell), and reduces the chance that improper signaling through CD4 would occur.

Another embodiment of the present invention relates to a compound which can regulate CA protein. The capsid protein of HIV (CA) can bind to cyclophilin A. Cyclophilin A has been found to function as an endonuclease that induces DNA fragmentation and binds several immunosuppressive drugs, one of which is cyclosporin A (CsA). Jurkat T cells incubated with CsA do not increase FasL expression upon T cell receptor (TCR) cross-linking. The cyclophilin A-binding activity of HIV-1 CA inhibits FasL expression in a similar manner. Therefore, CA expression protects cells from apoptosis by decreasing the availability of FasL or by preventing cyclophilin A from functioning as an endonuclease, thereby protecting the infected cell from DNA degradation.

Compounds useful as described herein includes, for example, compounds that are products of molecular diversity strategies (a combination of related strategies allowing the rapid construction of large, chemically diverse molecule libraries), rational drug design, natural products and compounds having partially defined signal transduction regulatory properties. Such a compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. Such a compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi, or Maulik et al., 1997, *Molecular Biotechnology:*  *Therapeutic Applications and Strategies,* Wiley-Liss, Inc., which are incorporated herein by reference in their entirety) or by rational drug design (see Maulik et al., ibid.).

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., ibid.

In a rational drug design procedure, the three-dimensional structure of a compound, such as a Vpr protein, can be analyzed by, for example, nuclear magnetic resonance (NMR) or X-ray crystallography. This three-dimensional structure can then be used to predict structures of potential compounds, such as putative regulatory compounds by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi). As used herein, a mimetope of a compound of the present invention refers to any compound that is able to mimic the activity of such a compound, often because the mimetope has a structure that mimics the compound. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Mimetopes can also be obtained by generating random samples of molecules, such as oligonucleotides, peptides or other organic molecules, and screening such samples by affinity chromatography techniques using the corresponding binding partner. Potential regulatory compounds of the present invention can also be identified using SELEX technology as described in, for example, PCT Publication Nos. WO 91/19813; WO 92/02536 and WO 93/03172 (which are incorporated herein by reference in their entireties).

It is within the scope of the present invention that regulation of an immunodeficiency virus protein which is a cellular inhibitor of apoptosis can be accomplished using an isolated nucleic acid molecule that encodes a protein capable of regulating the activity of an immunodeficiency virus protein. Such a nucleic acid molecule can be subcloned into an expression vector and transfected into a cell which is immunodeficiency virus infected or is at risk of becoming immunodeficiency virus infected. The expression vector comprises one or more transcription regulatory sequences that enable the nucleic acid molecule to be expressed in a cell. Standard conditions for cloning and expressing nucleic acid molecules are disclosed, for example, in Sambrook et al., 1989, *Molecular Cloning: A Laboratory Manual,* Cold Spring Harbor Labs Press. The reference Sambrook et al., ibid., is incorporated by reference herein in its entirety.

As used herein, an isolated nucleic acid molecule is a nucleic acid molecule that has been removed from its natural milieu (i.e., that has been subject to human manipulation).

As such, "isolated" does not reflect the extent to which the nucleic acid molecule has been purified. An isolated nucleic acid molecule can include DNA, RNA, or derivatives of either DNA or RNA. As used herein, reference to a nucleic acid molecule that encodes a protein capable of regulating the activity of an immunodeficiency virus protein or the like includes all nucleic acid sequences related to the coding region for such a protein such as regulatory regions that control production of the protein encoded by the nucleic acid molecule (such as, but not limited to, transcription, translation or post-translation control regions) as well as the coding region itself.

The present invention also includes a recombinant vector, or expression vector, which includes at least one isolated nucleic acid molecule that encodes a protein capable of regulating the activity of an immunodeficiency virus protein, inserted into any vector capable of delivering the nucleic acid molecule into a host cell. The vector can be either RNA or DNA, either prokaryotic or eukaryotic, and typically is a virus or a plasmid. Recombinant vectors can be used in the cloning, sequencing, and/or otherwise manipulating of such nucleic acid molecules. Preferred recombinant vectors are capable of replicating in the transformed cell.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. Transformed nucleic acid molecules of the present invention can remain extrachromosomal or can integrate into one or more sites within a chromosome of the transformed (i.e., recombinant) cell in such a manner that their ability to be expressed is retained.

A recombinant cell is preferably produced by transforming a host cell with one or more recombinant molecules, each comprising one or more nucleic acid molecules of the present invention operatively linked to an expression vector containing one or more regulatory sequences such as transcription regulatory sequences, translation control sequences, origins of replication, and other regulatory sequences that are compatible with the recombinant cell and that control the expression of nucleic acid molecules of the present invention. Transcription regulatory sequences are sequences which control the initiation, elongation, and termination of transcription. Particularly important transcription regulatory sequences are those which control transcription initiation, such as promoter, enhancer, operator and repressor sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell.

It will be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

One embodiment of the present invention relates to a cell based assay to identify a compound that regulates a cellular inhibitor of apoptosis in cells infected with an immunodeficiency virus. The method includes (a) contacting a putative regulatory compound with cells infected with an immunodeficiency virus under conditions in which, in the absence of said compound, apoptosis of the cells is inhibited; and (b) assessing the ability of the putative regulatory compound to regulate apoptosis in the cells, wherein a difference in the rate of apoptosis between infected cells contacted with the compound compared to infected cells not in contact with the compound indicates that the compound regulates a cellular inhibitor of apoptosis in cells infected with the immunodeficiency virus.

Suitable cells for use with the cell-based assay include any cell capable of being infected with an immunodeficiency virus. Preferably, cells for use with the present invention include mammalian cells, more preferably human and non-human primate cells. More preferred cells include immunodeficiency virus infected T lymphocytes and uninfected T lymphocytes, with human T cell lines, human T cell clones, with human T cell hybridomas being even more preferred.

The conditions under which a cell of the present invention (e.g., an HIV infected cell) is contacted with a putative regulatory compound, such as by mixing, are conditions in which the cell can undergo apoptosis if essentially no other regulatory compounds are present that would interfere with apoptosis. Effective conditions include, but are not limited to, appropriate medium, temperature, pH and oxygen conditions that permit cell growth. An appropriate medium is typically a solid or liquid medium comprising growth factors and assimilable carbon, nitrogen and phosphate sources, as well as appropriate salts, minerals, metals and other nutrients, such as vitamins, and includes an effective medium in which the cell can be cultured such that the cell can exhibit apoptosis. For example, for a mammalian cell, effective media is typically aqueous media comprising Dulbecco's modified Eagle's medium containing 10% fetal calf serum.

Cells of the present invention can be cultured in a variety of containers including, but not limited to tissue culture flasks, test tubes, microtiter dishes, and petri plates. Culturing is carried out at a temperature, pH and carbon dioxide content appropriate for the cell. Such culturing conditions are also within the skill in the art.

Methods for contacting a cell with a putative regulatory compound include electroporation, microinjection, cellular expression (i.e., using an expression system including naked nucleic acid molecules, recombinant virus, retrovirus expression vectors and adenovirus expression), use of ion pairing agents and use of detergents for cell permeabilization.

As used herein, the term "regulate" can be used interchangeably with the term "modulate". To "regulate" a molecule, a pathway, or a function of such a molecule or pathway, in the present invention refers to specifically controlling, or influencing the activity of such a molecule, pathway, or function, and can include regulation by activation, stimulation, inhibition, alteration or modification of such molecule, pathway or function. Preferably, compounds identified by methods of the present invention regulate apoptosis in a cell by inhibiting an inhibitor of apoptosis (i.e., an immunodeficiency virus apoptosis inhibitor protein), thereby inducing, or allowing, apoptosis in such a cell.

As used herein, the term "putative" refers to compounds which are being tested for regulatory activity and which have an unknown regulatory activity, at least with respect to the ability of such compounds to regulate apoptosis in an immunodeficiency virus infected cell.

A suitable amount of putative regulatory compound(s) is contacted with the cells in an amount that is sufficient to regulate the activity of an immunodeficiency virus apoptosis inhibitor protein inside the cell such that the regulation is detectable using a assessment method of the present invention. A preferred amount of putative regulatory compound(s) comprises between about 1 nM to about 10 mM of putative regulatory compound(s) per well of a 96-well plate.

The assay disclosed in the present invention involves contacting cells with the compound being tested for a sufficient time to allow for the compound to regulate a cellular inhibitor of apoptosis of cells (e.g., induce, or allow, apoptosis in an immunodeficiency virus infected cell). The period of contact with the compound being tested can be either the entire growth phase of the assay prior to scoring apoptosis or some smaller portion thereof. In one embodiment of the present invention, control cells are used to monitor the effectiveness of putative regulatory compounds at regulating a cellular inhibitor of apoptosis in immunodeficiency virus infected cells (e.g., HIV infected cells which are not contacted or incubated with a putative regulatory compound or non-infected cells incubated with or without HIV-infected cells and with or without a putative regulatory compound). As used herein, the term "contact period" refers to the time period during which cells are in contact with the compound being tested. The term "incubation period" refers to the entire time during which cells are allowed to grow prior to scoring. Thus, the incubation period includes all of the contact period and may include a further time period during which the compound being tested is not present but during which growth or apoptosis is continuing prior to scoring. A preferred incubation period is from about 1 to about 24 hours.

According to the present invention, the step of assessing (i.e., scoring) the ability of a putative regulatory compound to regulate apoptosis in a cell includes any method for measuring apoptosis in a cell. Such a method can include determining the extent of a morphological change in a cell. Such a morphological change can include, for example, progressive contraction of cell volume with the preservation of the integrity of cytoplasmic organelles and condensation of chromatin. Additionally, such a method can include determining the extent of DNA cleavage by gel electrophoresis, cell cycle analysis, or in situ tailing or nick translation. Additionally, such a method can include assessing membrane permeability by using dyes that bind RNA or DNA or Annexin V. Such assays for apoptosis are well known in the art; a few are described below.

For example, apoptosis of a cell can be assessed by using DNA binding dyes. These dyes are used to stain live cells for subsequent microscopic analysis or for subsequent flow cytometric analysis. When used for microscopic analysis of live cells, this technique assays nuclear morphology and membrane permeability. It provides one of the best ways of assessing apoptotic morphology in a quantitative manner and of discriminating live from dead cells and apoptotic from necrotic cells. When used for flow cytometric analysis, this technique assays membrane permeability. These dyes also bind DNA and are widely used to assay stages of the cell cycle by flow cytometry. Resting cells contain a 2N amount of DNA and form a "G1" peak, while cells in mitosis contain a 4N amount of DNA and form a 'G2' peak. DNA binding dyes have also been used at lower concentrations in fixed cells to identify an apoptotic "Go" peak below the resting G1 peak. This lower peak may be due to loss of DNA fragments with apoptosis or to altered conformation of apoptotic DNA. DNA laddering assays endonucleolytic cleavage of DNA into 200 base pair multimers. The scatter changes technique identifies apoptotic cells by their decreased forward scatter (due to cell shrinkage) and their increased side scatter (due to DNA condensation). This technique is easy; quantitative; can be done retrospectively on any cell sample that has been analyzed flow cytometrically, since all samples are routinely analyzed for forward and side scatter; can be done on fresh or fixed cells, and; can be done in conjunction with cell surface phenotyping or with immunofluorescent labeling of an intracellular marker. TUNEL or in situ nick translation takes advantage of the classic feature of apoptosis, DNA fragmentation. The enzyme terminal deoxynucleotidyl transferase (TdT) adds labeled nucleotides to the ends of nicked DNA. The label is then revealed in different ways depending on the application; a radioactive label allows development of grains over cells in fixed tissue, while a biotin-avidin conjugate allows immunohistochemical labeling of cells in tissue or flow cytometric analysis of cells in suspension. This technique is quantitative and allows for concurrent phenotyping of cells and for analysis of expressed RNAs by in situ hybridization.

Another embodiment of the present invention relates to an in vitro assay to identify a compound that regulates a cellular inhibitor of apoptosis in cells infected with an immunodeficiency virus. This method includes (a) contacting a putative regulatory compound with an immunodeficiency virus apoptosis inhibitor protein; and (b) assessing the ability of the putative regulatory compound to regulate the activity of the immunodeficiency virus apoptosis inhibitor protein.

According to the present invention, the step of contacting a putative regulatory compound with an immunodeficiency virus apoptosis inhibitor protein includes contacting a cell which expresses such an immunodeficiency virus apoptosis inhibitor protein with such a compound (e.g., an HIV infected cell or a recombinant cell expressing such an HIV apoptosis inhibitor protein) by the methods of contacting described above. Alternatively, the step of contacting can include contacting an isolated immunodeficiency virus apoptosis inhibitor protein directly with a putative regulatory reagent.

Preferably, compounds useful in methods of the present invention regulate an immunodeficiency virus apoptosis inhibitor protein by binding to an immunodeficiency virus apoptosis inhibitor protein and thereby effecting the activity of the inhibitor protein. Alternatively, regulation can be accomplished by a means including, but not limited to, degrading the immunodeficiency virus apoptosis inhibitor protein, inhibiting transcription of the nucleic acid molecule encoding the immunodeficiency virus apoptosis inhibitor protein, inhibiting translation of the immunodeficiency virus apoptosis inhibitor protein, inhibiting activation of the immunodeficiency virus apoptosis inhibitor protein, and inhibiting the interaction of the immunodeficiency virus apoptosis inhibitor protein with another protein involved in inhibition of apoptosis.

The ability of a putative regulatory compound to regulate the activity of said immunodeficiency virus apoptosis inhibitor protein can be assessed by determining apoptosis of a cell containing such an immunodeficiency virus apoptosis inhibitor protein as described above or by a method of directly measuring the activity of an immunodeficiency virus apoptosis inhibitor protein such as by measuring the ability of the immunodeficiency virus apoptosis inhibitor protein to bind to and/or effect the activation state of a molecule which is normally activated by such immunodeficiency virus apoptosis inhibitor protein or by measuring the transcription level or translation level of such immunodeficiency virus apoptosis inhibitor protein.

Another aspect of the present invention includes a method to limit infection by an immunodeficiency virus, which includes inhibiting an immunodeficiency virus protein which regulates apoptosis in cells. Such a method can be used to treat AIDS. As used herein, the treatment of AIDS (i.e., to treat AIDS) refers to a delay in or prevention of progression from asymptomatic immunodeficiency virus infection to AIDS, as well as to a decrease in the immunodeficiency virus viral load. Such treatment is useful in ameliorating the manifestations of immunodeficiency (opportunistic infections and malignancy) in individuals with AIDS. Compounds useful in methods of the present invention can be used in combination with an agent designed to inhibit immunodeficiency virus replication in infected cells, such as nucleoside analogues (e.g., AZT), non-nucleoside analogs, protease inhibitors, chemokine receptor inhibitors, antibodies specific for gp160, antibodies specific for gp120, CD4-gp160 protein complexes and/or gp120-CD4 protein complexes. In addition, compounds useful in methods of the present invention can be used in combination with an agent designed to inhibit uninfected bystander cell apoptosis by regulating a compound involved in non-immunodeficiency virus induced cellular apoptosis, including for example, a regulator of Lck (activated upon gp120/160 binding to CD4), CAMP, Protein kinase A (PKA; HIV induces the inhibitory CAMP/PKA pathway), cdc2 (premature cdc2 activation is required for apoptosis), cysteine proteases that induce apoptosis (e.g., ICE-like proteases), proteins of the TNF receptor family (including TNF, Fas, DR3, WSL-1), p53, Ras, Raf, MEKK1, Jun kinases, bcl-2 and oxygen radicals.

For example, one major pathway of apoptosis is mediated through the tumor necrosis family of receptors. Fas, in particular, has been extensively studied in recent years. Ligation of Fas by Fas ligand (Fas-L) present on the same or on a neighboring cell can induce either proliferation or apoptosis. $HIV^+$ individuals have a higher percentage of peripheral blood lymphocytes (PBL) positive for Fas expression and more Fas expressed per cell. More importantly, the $CD4^+$ and $CD8^+$ T cells from HIV-infected individuals are more susceptible to death induced by Fas ligation. Fas-induced death of CD4+ T cells has been found by some to correlate with disease stage, with more death seen in symptomatic than in asymptomatic individuals.

Lck is also correlated with enhanced HIV-induced apoptosis. The induction of apoptosis by gp120 binding to CD4 may be caused by an increase in Fas expression or by activation of the transcription factor AP-1, or the recruitment of Lck, causing improper activation of the cell.

An effective administration protocol (i.e., administering compounds useful in methods of the present invention in an effective manner) comprises suitable dose parameters and modes of administration that result in limiting infection by an immunodeficiency virus and/or prevention or treatment of AIDS. Effective dose parameters and modes of administration can be determined using methods standard in the art. Such methods include, for example, determination of survival rates, side effects (i.e., toxicity) and progression or regression of disease. For example, the effectiveness of dose parameters and modes of administration of a formulation of the present invention can be determined by assessing response rates. Such response rates refer to the percentage of treated patients in a population of patients that respond with either partial or complete remission.

The dose of compounds administered according to the present invention can be dependent on viral load or cell tropism, as well as differences in levels of expression of immunodeficiency virus genes encoding apoptosis regulator proteins (e.g. Vpr, Tat, Vif, Nef, Gag and Vpu). In particular, compounds useful in methods of the present invention are particularly useful when administered to transcriptionally active cells enabling elements in the long-terminal repeat of HIV to bind to activation-induced cellular transcription factors, such as nuclear factor of activated T cells (NF-AT) and nur-77 that direct viral transcription.

It will be obvious to one of skill in the art that the number of doses administered to an immunodeficiency virus infected patient is dependent upon the extent of the infection and the response of an individual to the treatment. For example, in the case of HIV-infection, a patient having a high titer of HIV may require more doses than a patient having lower titers. In some cases, however, a patient having a high titer of HIV may require fewer doses than a patient having lower titers, if the patient with the high titer responds more favorably to the therapeutic composition than the patient with the lower titer. Thus, it is within the scope of the present invention that a suitable number of doses, as well as the time periods between administration, includes any number required to cause regression of a disease.

A therapeutic composition comprising compounds of the present invention can be administered directly to a cell in vivo or ex vivo or systemically. Preferred methods of systemic administration, include intramuscular or intravenous injection. Intravenous injections can be performed using methods standard in the art. A therapeutic composition comprising compounds of the present invention can also comprise a pharmaceutically acceptable carrier. As used herein, a "pharmaceutically acceptable carrier" refers to any substance suitable as a vehicle for delivering a regulatory reagent of the present invention to a suitable in vitro or in vivo site of action. As such, carriers can act as a pharmaceutically acceptable excipient or formulation of a therapeutic composition containing compounds of the present invention. Preferred carriers are capable of maintaining compounds of the present invention in a form that is capable of enhancing progression of apoptosis of a cell. Examples of such carriers include, but are not limited to water, phosphate buffered saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a recipient, for example, esters or partial esters of fatty acids containing from about six to about twenty-two carbon atoms. Examples of esters include, caproic, octanoic, lauric, palmitic, stearic, linoleic, linolenic, olesteric, and oleic acids. Formulations of the present invention can be sterilized by conventional methods and/or lyophilized.

Useful carriers for compounds of the present invention include any artificial or natural lipid-containing target molecule, preferably cells, cellular membranes, liposomes, and micelles. Preferably, formulations of the present invention are administered in the form of liposomes or micelles. Liposome and micelles of the present invention are capable of delivering a regulatory reagent from the extracellular space of a cell to the intracellular space of a cell. Concentrations of a regulatory reagent of the present invention combined with a liposome or a micelle include concentrations effective for delivering a sufficient amount of compounds of the present invention to an infected cell such that the progression of apoptosis in such cell is enhanced. Lipid-based carriers of the present invention are particularly useful with embodiments of compounds of the present invention that comprise a nucleic acid molecule. Such delivery systems are known and have been successfully applied in the art and are discussed in Maulik et al., ibid., which is incorporated by reference herein in its entirety.

The following examples are provided for the purposes of illustration and are not intended to limit the scope of the present invention.

EXAMPLES

Example 1

The following example demonstrates the correlation between apoptosis and productive infection.

In order to determine the relative contributions of direct and indirect killing in HIV infection, tissue sections from lymph nodes of four children with perinatally acquired HIV infection were analyzed (Table 1). Patients were selected to reflect a range of CD4 counts. Sections from each biopsy were analyzed microscopically for HIV infection by RNA in situ hybridization. This analysis is specific for HIV viral and messenger RNA and thus detects HIV virions and productive infection. This method is described in Sambrook et al., ibid.

Tissues were fixed in formaldehyde within 30–60 min of surgical removal and embedded in paraffin. Duplicate sections were analyzed for each parameter (that is, HIV or SIV RNA, apoptosis, surface phenotype, or dual parameter analysis) from each lymph node. Before RNA in situ hybridization, in situ nick translation was performed. Briefly, paraffin was removed, and the sections were hydrated and digested briefly with proteolytic enzymes. Sections were then incubated in a reaction mixture containing terminal deoxynucleotidyl transferase (TdT) and biotinylated deoxyadenosine 5'-triphosphate (dATP). Control slides for each sample were incubated in an identical reaction mixture without TdT. Following the use of avidin-biotin phosphatase complex and new fuchsin reactions to deposit chromogen on the apoptotic nuclei, sections were hybridized with sense or antisense probes and run in duplicate. In situ hybridization was performed using radiolabelled RNA probes synthesized from five DNA templates, covering 90% of the HIV-1 or $SIV_{mac251}$ genome, subcloned into pGEM4. It is estimated that this technique has a sensitivity of detection of 10–50 HIV RNA copies, based on the observation that 2.8 silver grains are detected per free virion. HIV or SIV DNA was not detected by the antisense probes unless the DNA was first denatured. This was confirmed by the paucity of signal in control sections probed with HIV or SIV sense RNA. Grain counts of control sections probed with sense RNA were assigned a frequency distribution, and cells probed with antisense RNA with grain counts that fell outside the control distribution were classified as cells productively infected with HIV. The radiolabelled RNA β-actin probe was synthesized from a 1.3-kb DNA template and was subcloned into the EcoRI site of Bluescript KS. After hybridization and autoradiographic development for five days, slides were stained with hematoxylin, and examined by digital microscopy using a Peltier cooled charge coupled device (CCD; SpectraSource Inst.) mounted on a Zeiss Axiophot microscope, and processed using IPLab Spectrum software. The number of productively infected cells was similar with or without digestion of the sections with proteolytic enzymes before in situ hybridization. Immunohistochemical staining was done on duplicate subjacent sections using biotinylated polyclonal anti-CD3 antibody for detection of T cells, OPD4 for detection of a subset of $CD4^+$ T cells, or HAM 56 for detection of macrophages (data not shown), and developed using avidin-biotin phosphatase complex and new fuchsin reactions to deposit chromogen at the cell surface. All antibodies were purchased from Dako Corporation, Carpenteria, Calif.

In productive infection, HIV RNA is actively transcribed and translated, and virions assemble and bud from the surface of the infected cell. Sections were analyzed concurrently for apoptosis by in situ nick translation of the fragmented DNA, visualized as red nuclei. Some sections were also stained for surface expression of CD3, CD4, or a macrophage marker by using immunohistochemical techniques. The sections were analyzed by digital microscopy, using fluorescent filters to enhance the color differences between the two markers, and the fields shown are representative of each section.

Figure 2:
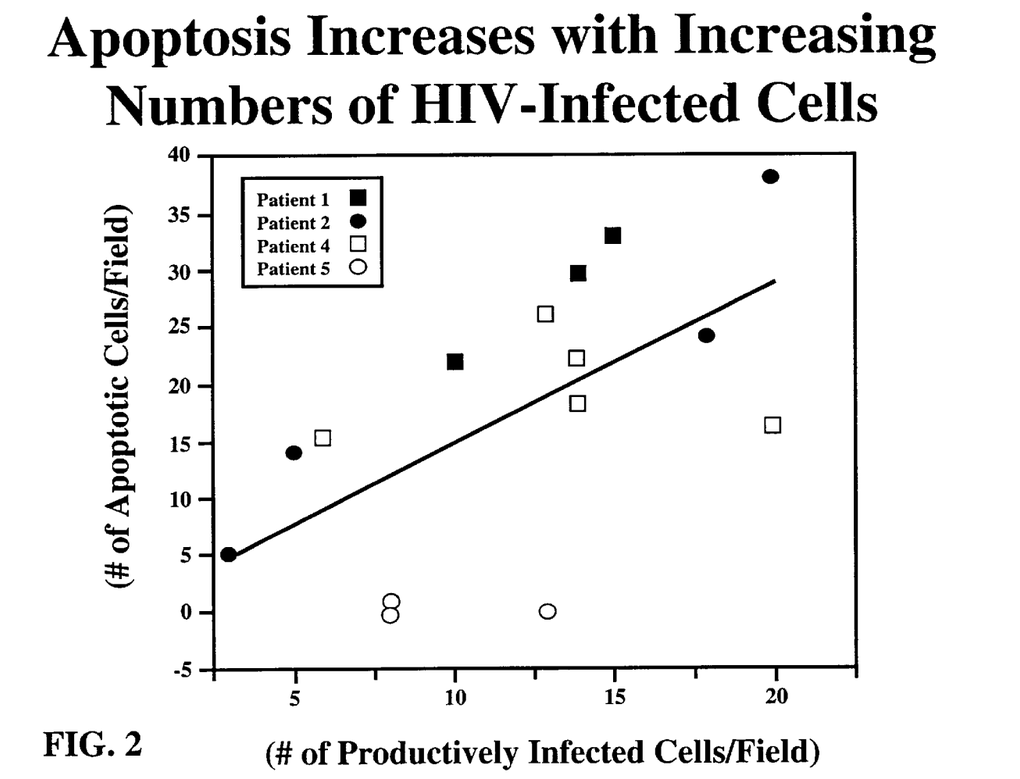
FIG. 2 is a linear regression plot showing the correlation between apoptosis and HIV infection in four patients.

Two distinct patterns of infection were seen within lymph nodes from infected children. One pattern was characterized by clouds of dispersed grains within germinal centers, similar to the pattern of virion binding to cytoplasmic processes of follicular dendritic cells (FDCs). Interspersed within these viral clouds were apoptotic cells, often in clusters, but in no case were the apoptotic cells productively infected. A second pattern was characterized by individual productively infected cells with HIV RNA at high copy number. In patients 1 and 3, apoptotic cells were also seen, often in clusters and often in close proximity to the productively infected cells, but again, in no case were the apoptotic cells productively infected. In patients 1 and 2 both patterns of HIV infection were seen. In patient 4, who had lost most of his $CD4^+$ cells (see Table 1), apoptotic cells were rarely found. As shown in FIG. 2, by simple linear regression, apoptosis and HIV infection were significantly related ($P=0.016$, $r^2=0.37$). This relationship remained significant ($P=0.0063$ for HIV, $r^2=0.83$) after accounting for multiple observations on individuals by analysis of covariance (data not shown).

TABLE 1

Case description of four children in different stages of HIV whose lymph nodes were analyzed for productive infection and apoptosis

| Patients[a] | Sex | Age (years) | Absolute CD4 count (cells per mm³) | Percent CD4 cells (%) | p24[b] | Therapy[c] |
|---|---|---|---|---|---|---|
| 1 | M | 3.46 | 2195 | 30 | 1343 | ZDV, DDI |
| 2 | F | 7.04 | 168 | 16 | 1029 | ZDV,DDI |
| 3 | M | 3.27 | 1122 | 19 | 6551 | 3TC |
| 4 | M | 2.36 | 11 | 1 | 249 | ZDV,DDI |

[a]These biopsies were obtained as part of a clinical protocol approved by the Institutional Review Board and with the informed consent of a parent or guardian. Patients 1–3 underwent lymph node biopsy for a protocol evaluating triple combination therapy with zidovudine, didanosine, and nevirapine. Data shown are from biopsies done before nevirapine therapy. None of these patients had clinically significant lymphadenopathy or opportunistic infection at the time of biopsy. Patient 4 biopsied because of generalized adenopathy and pneumonitis. Bronchoalveolar lavage was negative for *Pneumocystis carinii* pneumonia, but positive for cytomegalovirus. The lymph node of patient 4 demonstrated a polymorphous, polyclonal B-cell infiltrate and was positive for Epstein-Barr virus by in situ hybridization.
[b]Immune complex-dissociated p24 assay.
[c]ZDV, zidovudine; DDI, didanosine; 3TC, 3-thiacytidine.

Example 2

The following example demonstrates that HIV- or SIV-infected lymph node cells are rarely apoptotic.

As noted in Example 1, infected and apoptotic cells were often seen in close proximity, but in no case, in these sections, were apoptosis and productive infection seen in the same cell. A total of 219 fields were analyzed, each measuring 200 µm in diameter, with a total of 1,031 apoptotic cells and 696 infected cells, none of which appeared both apoptotic and infected. Thus, less than 0.10% of red (apoptotic) cells had green grains (productive infection) and less than 0.14% cells with green grains (productive infection) were red (apoptotic). In other sections from these children, from one additional child, and from four adult patients, apoptosis and productive infection were seen only rarely in the same cell. Thus, productive infection with HIV does not necessarily induce apoptotic cell death.

These data were confirmed in lymph node sections from an SIV-infected rhesus macaque infant. This animal was infected perinatally by oral inoculation of virus and was analyzed at postmortem examination using the following method. The animal studied (93-9) and the oral infection protocol using SIVmac251 have been described in the art. The animal was killed at 6 months of age with advanced disease, characterized by severe anemia, thrombocytopenia, loss of CD4⁺ T cells, and severe glomerulonephritis. Tissues were processed as described above.

The results indicated that apoptosis and productive infection were seen in different cells. Although the frequency of apoptotic infected cells in these sections was as low as noted above, it was rare to find examples of such cells. Thus, productive infection with SIV does not necessarily induce apoptotic cell death.

Taken together, this analysis suggests that while apoptotic nuclei are detected (in some cases in large numbers) in infected lymph nodes, apoptosis of productively infected cells is a rare event.

Example 3

The following example shows viral RNA and apoptosis in secondary follicles.

The apoptotic cell death seen in the HIV- and SIV-infected lymph nodes occurred in uninfected bystander cells. Some of the apoptotic cells were found in the paracortical or T cell-rich regions of the lymph nodes. These were also the regions in which individual productively infected cells were found. Interestingly, close apposition of an apoptotic and an infected cell was occasionally seen. However, in all nodes analyzed (perinatally HIV-infected children, a perinatally SIV-infected macaque, and HIV-infected adults) displayed localization of the majority of apoptotic cells in the secondary follicles, specifically to the apical light zone of the follicles, a region known to be rich in B cells, activated CD4⁺ (and with viral infection, CD8⁺) T cells, and FDCs. Also localized to this apical light zone of secondary follicles were the clouds of dispersed grains, likely identifying virions bound to the cytoplasmic processes of FDCs. In the children studied (Table 1), patients 1, 2 and 3 had, on average, 11.9±4.5 apoptotic cells in fields having viral clouds, versus only 1.8±0.3 apoptotic cells in fields lacking viral clouds. Patient 4 had no viral clouds and no apoptotic cells, possibly because of advanced disease and an almost complete absence of CD4⁺ T cells (Table 1). Thus, viral RNA and apoptotic cells were predominantly colocalized in the secondary follicles of HIV-and SIV-infected lymph nodes.

By concurrent staining for apoptosis and surface phenotype, the results indicate that some of the apoptotic cells are CD4⁺ T cells. Thus, apoptosis in the apical light zone of the secondary follicles of HIV- or SIV-infected nodes is occurring in activated CD4⁺ (or CD8⁺) T cells upon interaction with viral antigens presented by follicular B cells or with virus bound to FDCs.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to identify a compound that is a modulator of apoptosis in CD4⁺ T lymphocytes infected with human immunodeficiency virus-1 (HIV-1), said method comprising the steps of:

(a) contacting a putative modulatory compound with HIV-1-infected CD4⁺ T lymphocytes, wherein said HIV-1 is capable of expressing a functional HIV-1 protein having apoptotic modulatory activities selected from the group consisting of HIV-1 Vpr and HIV-1 Nef, under conditions in which, in the absence of said compound, apoptosis of said HIV-1-infected CD4⁺ T lymphocytes is inhibited;

(b) assessing the effects of said compound on nef and vpr gene expression and function employing a determinative step selected from the group consisting of: (1) measuring the ability of said compound to inhibit nef and/or vpr transcription; (2) measuring the ability of said compound to inhibit translation of nef and/or vpr; (3) measuring the ability of said compound to degrade said HIV-1 protein; and, (4) measuring the ability of said compound to inhibit a biochemical activity of said HIV-1 protein;

(c) assessing the effects of said compound on apoptosis by employing a determinative step selected from the group consisting of: (1); (2); (3); and (4); and, (d) comparing the results obtained in steps (b) and (c) with those obtained from HIV-1-infected CD4⁺ T lymphocytes not in contact with said putative modulatory compound;

wherein a reduction in nef or vpr gene expression or function as determined in step (b), and an increase in apoptosis as determined in step (c), as compared to T lymphocytes not in contact with said putative modulatory compound, indicates that said compound is a modulator of apoptosis in HIV-1-infected $CD4^+$ T lymphocytes.

2. The method of claim 1, wherein said step (c) of assessing further comprises a step selected from the group consisting of (1) determining the extent of a morphological change in a cell selected from the group consisting of progressive contraction of cell volume with the preservation of the integrity of cytoplasmic organelles and condensation of chromatin; (2) determining the extent of DNA cleavage; and (3) determining membrane permeability.

3. The method of claim 1, wherein said HIV-1 protein is Vpr protein.

4. The method of claim 1, wherein said HIV-1 protein is Nef protein.

5. A method to identify a compound that is a putative modulator of apoptosis in $CD4^+$ T lymphocytes infected with human immunodeficiency virus-1 (HIV-1), said method comprising the steps of:

(a) contacting a putative modulatory compound with an HIV-1 protein having apoptotic modulatory activities selected from the group consisting of HIV-1 Vpr and HIV-1 Nef;

(b) assessing the effects of said compound on said HIV-1 protein by employing a determinative step selected from the group consisting of: (1) measuring the ability of said compound to degrade said HIV-1 protein; and, (2) measuring the ability of said compound to inhibit a biochemical activity of said HIV-1 protein;

wherein an increase in the degradation of said HIV-1 protein and/or a reduction in the biochemical activity of said HIV-1 protein as determined in step (b) as compared to said HIV-1 protein not in contact with said putative modulatory compound, indicates that said compound is a putative modulator of apoptosis in HIV-1-infected $CD4^+$ T lymphocytes.

6. The method of claim 5, wherein said HIV-1 protein is Vpr protein.

7. The method of claim 5, wherein said HIV-1 protein is Nef protein.

* * * * *